United States Patent
Teng et al.

(10) Patent No.: US 7,288,545 B2
(45) Date of Patent: Oct. 30, 2007

(54) PIPERAZINEDIONE COMPOUNDS

(75) Inventors: Che-Ming Teng, Taipei (TW); Hui-Po Wang, Taipei (TW); Eric I. C. Li, Tainan (TW); On Lee, Taipei (TW); Jih-Hwa Guh, Taipei (TW); Huei-Ting Chen, Taipei (TW); Ya-Bing Fan, Taipei (TW); Ya-Lan Chen, Tainan (TW)

(73) Assignee: AngioRx Corporation, Taipei (TW)

( * ) Notice: Subject to any disclaimer, the term of this patent is extended or adjusted under 35 U.S.C. 154(b) by 246 days.

(21) Appl. No.: 10/689,865

(22) Filed: Oct. 20, 2003

(65) Prior Publication Data

US 2004/0132738 A1 Jul. 8, 2004

Related U.S. Application Data

(63) Continuation-in-part of application No. 09/851,077, filed on May 8, 2001, now Pat. No. 6,635,649.

(60) Provisional application No. 60/304,191, filed on May 9, 2000, now abandoned.

(51) Int. Cl.
*A61K 31/496* (2006.01)
*C07D 405/14* (2006.01)

(52) U.S. Cl. .................. 514/253.11; 514/253.12; 514/253.01; 514/255.02; 514/249; 544/360; 544/364; 544/349; 544/350; 544/385

(58) Field of Classification Search .............. 544/360, 544/364; 514/253.11, 253.12
See application file for complete search history.

(56) References Cited

U.S. PATENT DOCUMENTS

| | | | |
|---|---|---|---|
| 4,940,709 A | 7/1990 | Shimazaki et al. | 514/253 |
| 5,700,804 A | 12/1997 | Collins et al. | 514/255 |
| 5,902,812 A | 5/1999 | Brocchini et al. | 514/253 |
| 6,635,649 B2 * | 10/2003 | Teng et al. | 514/253.11 |

FOREIGN PATENT DOCUMENTS

| | | |
|---|---|---|
| JP | 59073574 | 4/1984 |
| JP | 08151366 | 6/1996 |
| WO | WO94/04512 | 3/1994 |
| WO | 95/21832 | 8/1995 |
| WO | 01/95858 A2 * | 12/2001 |

OTHER PUBLICATIONS

Bavykina et al., "Synthesis of Diketopiperazines Related to Cyclohistidylproline", Zhurnal Obschchei Khimii, 60:148-152, 1990, XP009008684.
Hayashi, et al. *Total Synthesis of Anti-microtubule Diketopiperzine Derivatives: Phenyahistin and Aurantiamine.* J. Org. Chem. Dec. 1, 2000;65(24):8402-5.
Kanoh, et al. *Synthesis and Biological Activities of Phenylahistin Derivatives.* Bioorg. Med. Chem. Jul. 1999; 7(7): 1451-7.
Kanoh, et al. *Antitumor Activity of Phenylahistin In Vitro and In Vivo.* Biosci. Biotechnol. Biochem. Jun. 1999; 63(6):1130-3.
Kanoh, et al. *(-)-Phenylahistin Arrests Cells In Mitosis By Inhibiting Tubulin Polymerization..* J. Antibiot (Tokyo). Feb. 1999;52(2):134-41.
Kondoh et al., Journal of Antibiotics, 51:801-804, 1998.
Kunishima et al., J. Am Chem. Soc. 121:4722-4723, 1999.
Matsunaga et al., "Isolation and Structure of Citreoindole, a New Metabolite of Hybrid Strain KO 0052 Derived from Penicillium Citreo-viride B. IFO 6200 and 4692", Tetrahedron Letters 32:6883-6884, 1991, XP009008691.
Scakler et al., "NMR Studies on the Conformation of Cyclodipeptides with Two Identical L-aromatic Amino Acid Residues in Solutions—cyclo[-L-5(OH)Trip-L-5(OH)Trp] and cyclo[-L-Phe-L-Phe]", Int. J. Peptide Protein Res. 38:8-14, 1991, XP009008689.
Saito et al., "Synthetic Approaches Toward Ecteinascidins. Part 1. Preparation of an (e)-2-arylidene-3-benzyl-1,5-imino-3-benzazocin-4-One Having a Protected Phenol in the E-ring", J. Chem. Soc., Perkin Trans. 53-69, 1997, XP-002237321.
Scakler et al., "NMR Studies on the Conformation of Cyclodipeptides with Two Identical L-aromatic Amino Acid Residues in Solutions—cyclo[-L-5(OH)Trip-L-5(OH)Trp] and cyclo[-L-Phe-L-Phe]", Int. J. Peptide Protein Res. 38:8-14, 1991, XP009008689.
Sheinblatt, "NMR Studies on the Conformation of Aromatic Cyclodipeptides with Two Non-identical L-Aromatic Amino-acid Residues in Solution: Cyclo-[L-5(MeO)Trp-L-Tyr(Me)]", J. Chem. Soc., Perkin Trans. 127-132, 1990, XP009008690.
Takayama et al., "Sterochemical Studies on the Uncaria Alkaloid, 3-Oxo-7-hydroxy-3,7-secorhynchophylline: The Absolute Configuration of 3-Hydroxyoxindole Derivatives", Tetrahedron 55:6841-6846, 1999. * cited by examiner

*Primary Examiner*—Emily Bernhardt
(74) *Attorney, Agent, or Firm*—Occhiuti Rohlicek & Tsao

(57) ABSTRACT

This invention relates to a method for treating an angiogenesis-related disease. The method includes administering to a subject in need thereof an effective amount of a piperazinedione compound having the formula:

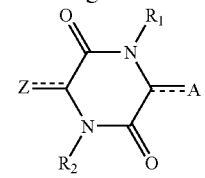

In the above formula, each of ===== and -----, independently, is a single bond or a double bond; A is H or CH($R^a R^b$) when ----- is a single bond, or C($R^a R^b$) when ----- is a double bond; Z is CH($R^c R^d$) when ===== is a single bond, or C($R^c R^d$) when ===== is a double bond; each of $R_1$ and $R_2$, independently, is H, C(O)$R^e$, C(O)O$R^e$, C(O)N$R^e R^f$, or SO$_2R^e$; and each of $R^a$, $R^b$, $R^c$, $R^d$, $R^e$, and $R^f$, independently, is H, $C_1$-$C_6$ alkyl, aryl, heteroaryl, $C_3$-$C_8$ cycloalkyl, or $C_3$-$C_8$ heterocycloalkyl; or $R^a$ and $R^b$ taken together are $C_3$-$C_8$ cycloalkyl, $C_3$-$C_8$ heterocycloalkyl, aryl, or heteroaryl; or $R_1$ and $R^a$ or $R_1$ and $R^b$ taken together are $C_3$-$C_8$ cycloalkyl, $C_3$-$C_8$ heterocycloalkyl, aryl, or heteroaryl; provided that one of $R^c$ and $R^d$ is aryl or heteroaryl.

5 Claims, No Drawings

PIPERAZINEDIONE COMPOUNDS

CROSS REFERENCE TO RELATED APPLICATION

This application is a continuation-in-part of U.S. application Ser. No. 09/851,077, filed on May 8, 2001, now U.S. Pat. No. 6,635,649, which claims priority to U.S. Provisional Application 60/304,191, filed on May 9, 2000, now abandoned, which was converted from U.S. Utility application Ser. No. 09/567,271.

BACKGROUND

Angiogenesis, formation of new blood vessels, occurs in human bodies to restore blood flow to injured tissues. It is controlled by various positive and negative regulatory factors. Excessive blood vessel growth may be triggered by certain pathological conditions, such as cancer, age-related macular degeneration, rheumatoid arthritis, retinopathy, and psoriasis. See Martin et al., *Carcinogenesis* Advanced Access published May 9, 2003; Soubrane et al., *Presse. Med.*, (2002) 31(27):1282; Gravallese et al., *Ann. Rheum. Dis.*, (2003) 62:100; Lahdenranta et al., *PNAS* 98(18): 10368; Xia et al., *Blood*, 2003, 102(1):161. As a result of excessive angiogenesis, new blood vessels feed diseased tissues and destroy normal tissues. For example, new vessels allow tumor cells to migrate into the blood circulation system and lodge in other organs.

Angiogenesis occurs via a series of steps, including division and migration of endothelial cells, which form the wall of blood vessels. More than 15 proteins are known to activate endothelial cells' growth and movement, such as angiogenin, epidermal growth factor, estrogen, fibroblast growth factor, interleukin 8, prostaglandins E1 and E2, tumor necrosis factor, vascular endothelium growth factor, and granulocyte colony-stimulating factor.

Angiogenesis can be suppressed by inhibiting any angiogenic stimulus. Compounds that effectively inhibit angiogenesis are candidates for treating angiogenesis-related disorders.

SUMMARY

This invention is based on the unexpected discovery that certain piperazinedione compounds inhibit angiogenesis.

In one aspect, this invention features a method for treating an angiogenesis-related disease. The method includes administering to a subject in need thereof an effective amount of a piperazinedione compound having the formula:

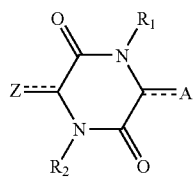

In the above formula, each of ----- and -----, independently, is a single bond or a double bond; A is H or CH($R^a R^b$) when ----- is a single bond, or C($R^a R^b$) when ----- is a double bond; Z is CH($R^c R^d$) when ----- is a single bond, or C($R^c R^d$) when ----- is a double bond; each of $R_1$ and $R_2$, independently, is H, C(O)$R^e$, C(O)O$R^e$, C(O)N$R^e R^f$, or SO$_2 R^e$; and each of $R^a$, $R^b$, $R^c$, $R^d$, $R^e$, and $R^f$, independently, is H, $C_1$-$C_6$ alkyl, aryl, heteroaryl, $C_3$-$C_8$ cycloalkyl, or $C_3$-$C_8$ heterocycloalkyl; or $R^a$ and $R^b$ taken together are $C_3$-$C_8$ cycloalkyl, $C_3$-$C_8$ heterocycloalkyl, aryl, or heteroaryl; or $R_1$ and $R^a$ or $R_1$ and $R^b$ taken together are $C_3$-$C_8$ cycloalkyl, $C_3$-$C_8$ heterocycloalkyl, aryl, or heteroaryl; provided that one of $R^c$ and $R^d$ is aryl or heteroaryl.

A subset of the above-described piperazinedione compounds features that both ----- and ----- are double bonds. In these compounds, $R^c$ is 2-pyridyl substituted with arylalkoxy at position 5 and $R^d$ is H. Another subset of the piperazinedione compounds features that both ----- and ----- are single bonds. In these compounds, $R^c$ is 2-pyridyl substituted with arylalkoxy at position 5 and $R^d$ is H.

"Treatment" refers to administering one or more piperazinedione compounds to a subject, who has an angiogenesis-related disease, a symptom of such a disease, or a predisposition toward such a disease, with the purpose to confer a therapeutic effect, e.g., to cure, relieve, alter, affect, ameliorate, or prevent the angiogenesis-related disease, the symptom of it, or the predisposition toward it. Examples of angiogenesis-related diseases include cancer, age-related macular degeneration, rheumatoid arthritis, retinopathy, psoriasis, cardiovascular diseases, chronic inflammation, diabetes, endometriosis, and adiposity. "An effective amount" refers to the amount of one or more piperazinedione compounds described above that is required to confer a therapeutic effect on a treated subject. A piperazinedione compound described above can be administered with one or more other therapeutic agents (e.g., cytotoxic or cytostastic agents) at the same time or at different times during the period of a treatment.

The term "alkyl" refers to a saturated, linear or branched, non-aromatic hydrocarbon moiety, such as CH$_3$, —CH$_2$—, or branched $C_3 H_7$. The term "cycloalkyl" refers to a saturated cyclic hydrocarbon moiety, such as cyclohexyl. The term "heterocycloalkyl" refers to a saturated non-aromatic cyclic moiety having at least one ring heteroatom, such as 4-tetrahydropyranyl. The term "aryl" refers to a hydrocarbon moiety having one or more aromatic rings. Examples of an aryl moiety include phenyl, phenylene, naphthyl, naphthylene, pyrenyl, anthryl, and phenanthryl. The term "heteroaryl" refers to a moiety having one or more aromatic rings that contain at least one heteroatom. Examples of a heteroaryl moiety include furyl, furylene, fluorenyl, pyrrolyl, thienyl, oxazolyl, imidazolyl, thiazolyl, pyridyl, pyrimidinyl, quinazolinyl, quinolyl, isoquinolyl and indolyl. The term "arylalkoxy" refers to a moiety having an oxygen radical and at least one alkyl moiety substituted with aryl or heteroaryl, such as benzyloxy (BnO) or pyridinylmethyloxy.

Alkyl, cycloalkyl, heterocycloalkyl, aryl, heteroaryl, and arylalkoxy mentioned herein include both substituted and unsubstituted moieties. Examples of substituents for cycloalkyl, heterocycloalkyl, aryl, heteroaryl, and arylalkoxy include $C_1$-$C_{10}$ alkyl, $C_2$-$C_{10}$ alkenyl, $C_2$-$C_{10}$ alkynyl, $C_3$-$C_8$ cycloalkyl, $C_5$-$C_8$ cycloalkenyl, $C_1$-$C_{10}$ alkoxy, aryl, aryloxy, heteroaryl, heteroaryloxy, amino, $C_1$-$C_{10}$ alkylamino, $C_1$-$C_{20}$ dialkylamino, arylamino, diarylamino, hydroxyamino, alkoxyamino, $C_1$-$C_{10}$ alkylsulfonamide, arylsulfonamide, hydroxy, halogen, thio, $C_1$-$C_{10}$ alkylthio, arylthio, cyano, nitro, mercapto, carbamido, carbamoyl, thioureido, thiocyanato, sulfonamido, acyl, acyloxy, carboxyl, and carboxylic ester. Examples of substituents for alkyl include all of the above substitutents except $C_1$-$C_{10}$ alkyl, $C_2$-$C_{10}$ alkenyl, and $C_2$-$C_{10}$ alkynyl. Cycloalkyl and heterocycloalkyl can also be fused with aryl or heteroaryl.

In another aspect, this invention features piperazinedione compounds of the same formula shown above. Referring to this formula, each of ----- and -----, independently, is a single bond or a double bond; A is H or CH(R$^a$R$^b$) when ----- is a single bond, or C(R$^{a'}$R$^{b'}$) when ----- is a double bond; Z is CH(R$^c$R$^d$) when ----- is a single bond, or R$_3$O—(Ar)—C(R$^e$) when ----- is a double bond; in which Ar is pyridyl linked to B at position 2; and R$_3$ is C$_1$-C$_6$ alkyl substituted with aryl, C(O)R$^f$, or S(O)R$^f$; each of R$_1$ and R$_2$, independently, is H or C(O)R$^g$; R$^a$ is H, C$_1$-C$_6$ alkyl, aryl, heteroaryl, C$_3$-C$_8$ cycloalkyl, or C$_3$-C$_8$ heterocycloalkyl; R$^b$ is H, C$_1$-C$_6$ alkyl, or aryl; or R$^a$ and R$^b$ taken together are C$_3$-C$_8$ cycloalkyl, C$_3$-C$_8$ heterocycloalkyl, aryl, or heteroaryl; or R$_1$ and R$^a$ or R$_1$ and R$^b$ taken together are C$_3$-C$_8$ cycloalkyl, C$_3$-C$_8$ heterocycloalkyl, aryl, or heteroaryl; R$^{a'}$ is benzo[1,3]dioxol-5-yl, 4-benzyloxy-2-pyridyl, phenyl, or phenyl substituted with hydroxy or arylalkyoxy; R$^{b'}$ is H, C$_1$-C$_6$ alkyl, or aryl; or R$^{a'}$ and R$^{b'}$ taken together are C$_3$-C$_8$ cycloalkyl, C$_3$-C$_8$ heterocycloalkyl, aryl, or heteroaryl; or R$_1$ and R$^{a'}$ or R$_1$ and R$^{b'}$ taken together are C$_3$-C$_8$ cycloalkyl, C$_3$-C$_8$ heterocycloalkyl, aryl, or heteroaryl; provided that if R$^{a'}$ is phenyl, R$_3$ is C(O)R$^{d'}$ or S(O)R$^{d'}$; R$^c$ is aryl or heteroaryl; R$^d$ is H, C$_1$-C$_6$ alkyl, aryl, heteroaryl, C$_3$-C$_8$ cycloalkyl, or C$_3$-C$_8$ heterocycloalkyl; in which aryl is substituted with one or more substituents selected from the group consisting of halogen, hydroxy, amino, alkylamino, arylamino, dialkylamino, diarylamino, cyano, nitro, mercapto, carbamido, carbamoyl, carboxyl, thioureido, thiocyanato, sulfonamido, C$_1$-C$_6$ alkyl, C$_2$-C$_6$ alkenyl, aryl, and aryloxy; and heteroaryl and C$_3$-C$_8$ heterocycloalkyl are substituted with one or more substituents selected from the group consisting of halogen, hydroxy, amino, alkylamino, arylamino, dialkylamino, diarylamino, cyano, nitro, mercapto, carbamido, carbamoyl, carboxyl, thioureido, thiocyanato, sulfonamido, C$_2$-C$_6$ alkenyl, C$_1$-C$_6$ alkoxy, and aryloxy; each of R$^e$ and R$^f$, independently, is H, C$_1$-C$_6$ alkyl, aryl, or arylamino; and R$^g$ is H, C$_1$-C$_6$ alkyl, or aryl.

A subset of the just-described piperazinedione compounds features that both ----- and ----- are double bonds. In these compounds, R$^{a'}$ is benzo[1,3]dioxol-5-yl, 4-benzyloxy-2-pyridyl, phenyl, or phenyl substituted with hydroxy or benzyloxy; R$^{b'}$ is H; R$_e$ is H; and R$_3$ is benzyl. Another subset of the piperazinedione compounds features that both ----- and ----- are single bonds. In these compounds, R$_c$ is 2-pyridyl substituted with arylalkoxy at position 5; R$^d$ is H; R$^a$ is aryl or heteroaryl; and R$^b$ is H.

In a further aspect, this invention features a pharmaceutical composition that contains an effective amount of at least one of the above-mentioned piperazinedione compounds and a pharmaceutically acceptable carrier.

Shown below are exemplary compounds, compounds 1-35, can be used by the method of this invention.

Compound 1

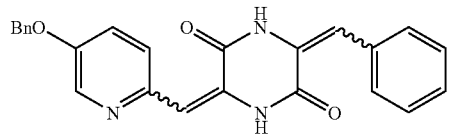

-continued

Compound 2

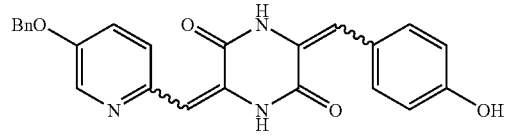

Compound 3

Compound 4

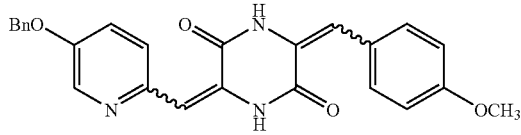

Compound 5

Compound 6

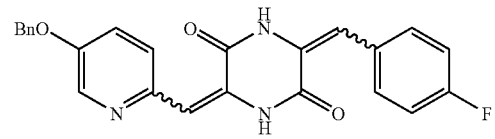

Compound 7

Compound 8

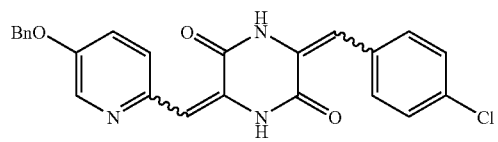

Compound 9

Compound 10

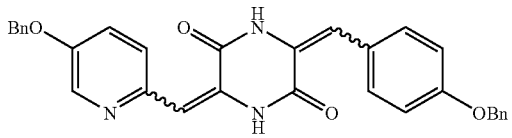

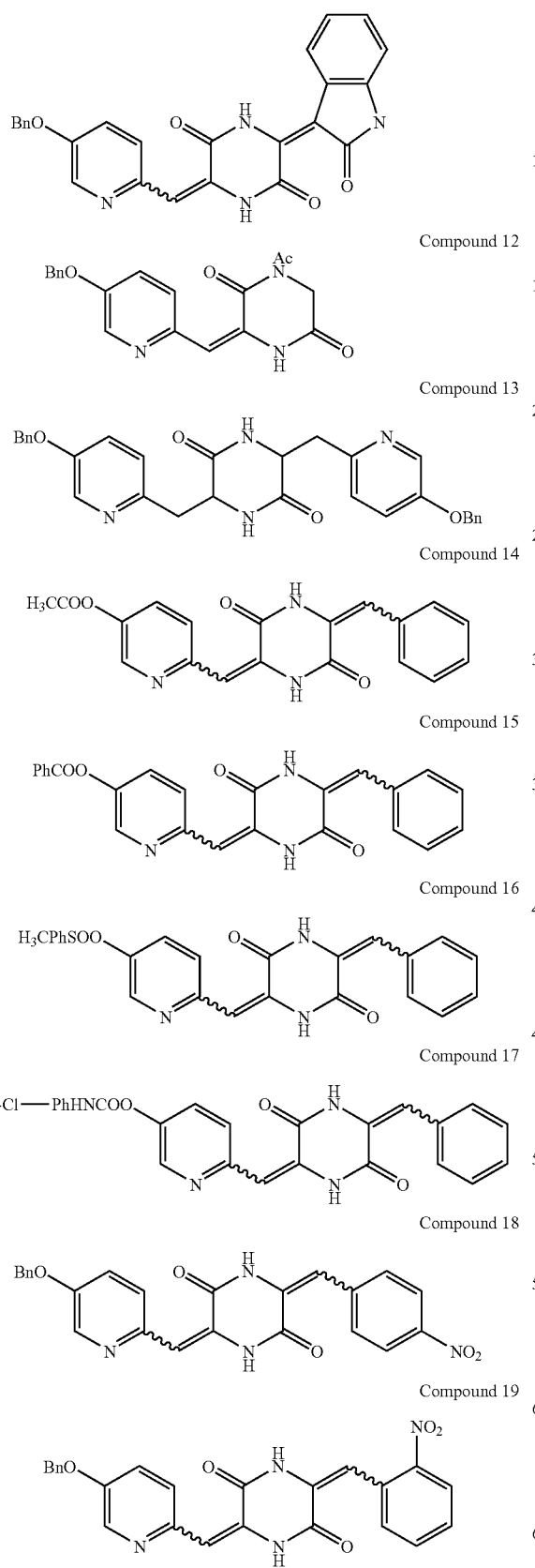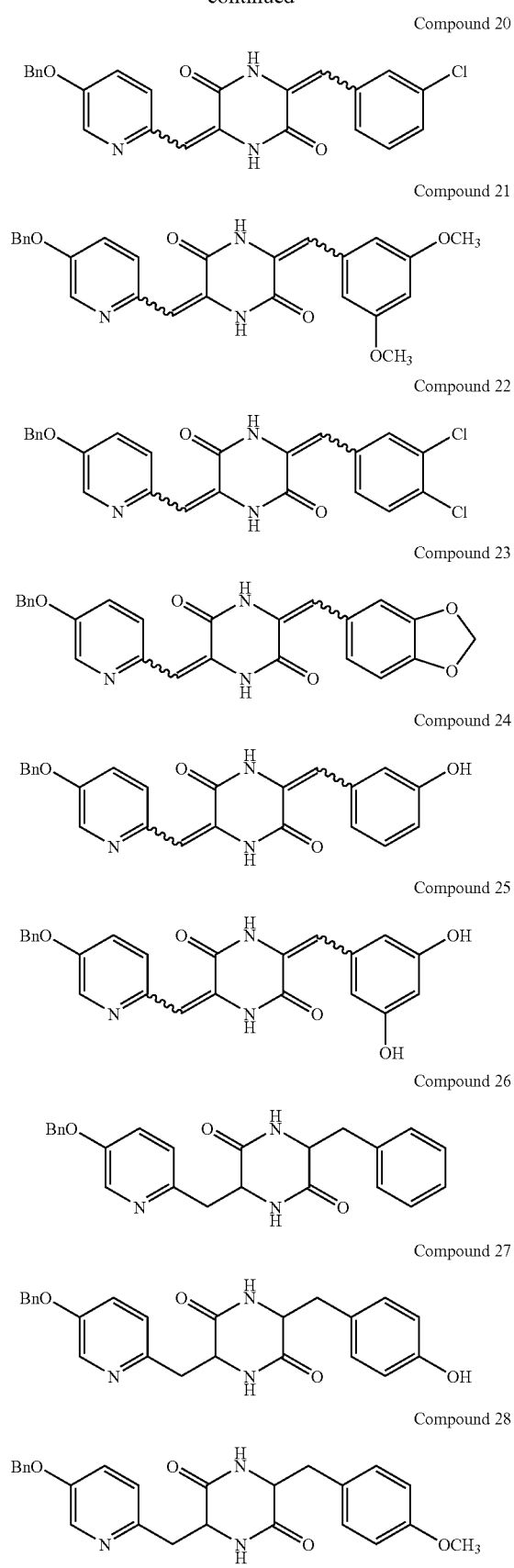

Compound 29
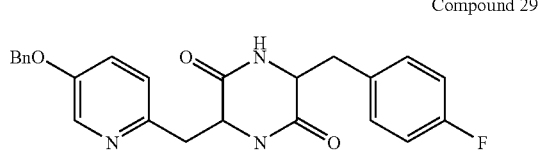

Compound 30
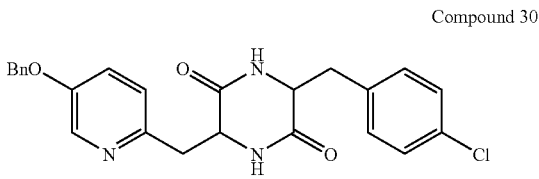

Compound 31
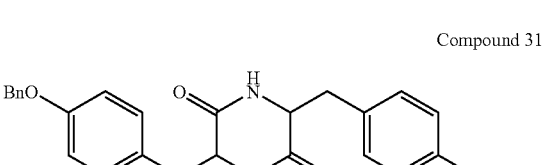

Compound 32
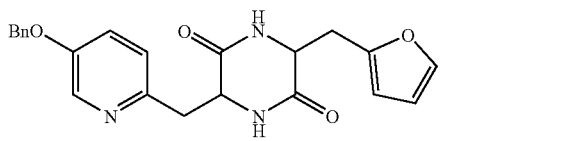

Compound 33
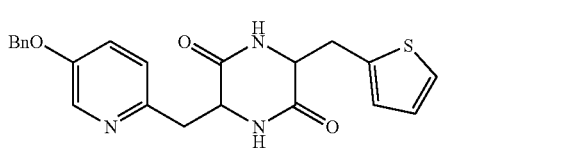

Compound 34
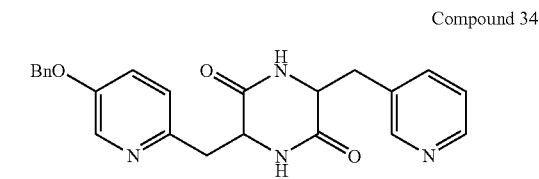

Compound 35
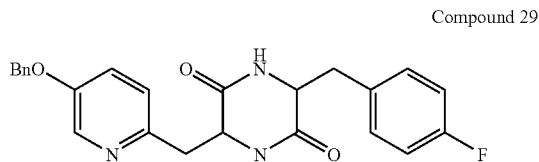

The piperazinedione compounds described above include the compounds themselves, as well as their salts and their prodrugs, if applicable. A salt, for example, can be formed between an anion and a positively charged group (e.g., amino) on a piperazinedione compound. Suitable anions include chloride, bromide, iodide, sulfate, nitrate, phosphate, citrate, methanesulfonate, trifluoroacetate, and acetate. Likewise, a salt can also be formed between a cation and a negatively charged group (e.g., carboxylate) on a piperazinedione compound. Suitable cations include sodium ion, potassium ion, magnesium ion, calcium ion, and an ammonium cation such as tetramethylammonium ion. Examples of prodrugs include esters and other pharmaceutically acceptable derivatives, which, upon administration to a subject, are capable of providing active piperazinedione compounds.

Also within the scope of this invention is a composition containing one or more of the piperazinedione compounds described above for use in treating an angiogenesis-related disease, and the use of such a composition for the manufacture of a medicament for the just-mentioned treatment.

The details of one or more embodiments of the invention are set forth in the description below. Other features, objects, and advantages of the invention will be apparent from the description and from the claims.

DETAILED DESCRIPTION

The piperazinedione compounds described above can be prepared by methods well known in the art, as well as by the synthetic routes disclosed herein. For example, one can react a piperazine-2,5-dione compound with a heteroaryl formaldehyde to produce an intermediate heteroaryl-methylidene-piperazine-2,5-dione. The intermediate can then be reduced to heteroaryl-methyl-piperazine-2,5-dione (a compound of this invention), or treated with a ketone or another formaldehyde, followed by a base treatment, to produce a mixture of piperazinedione isomers, which are cis- or trans- or E- or Z-double bond isomeric forms. The desired isomeric product can be separated from others by high pressure liquid chromatography (HPLC). If preferred, proper functional groups can be introduced into the heteroaryl ring by further modifications. Alternatively, a desired reduced product can be obtained by reacting the product with a reducing agent.

Shown below is a scheme that depicts the synthesis of the 35 piperazinedione compounds mentioned in the Summary section above.

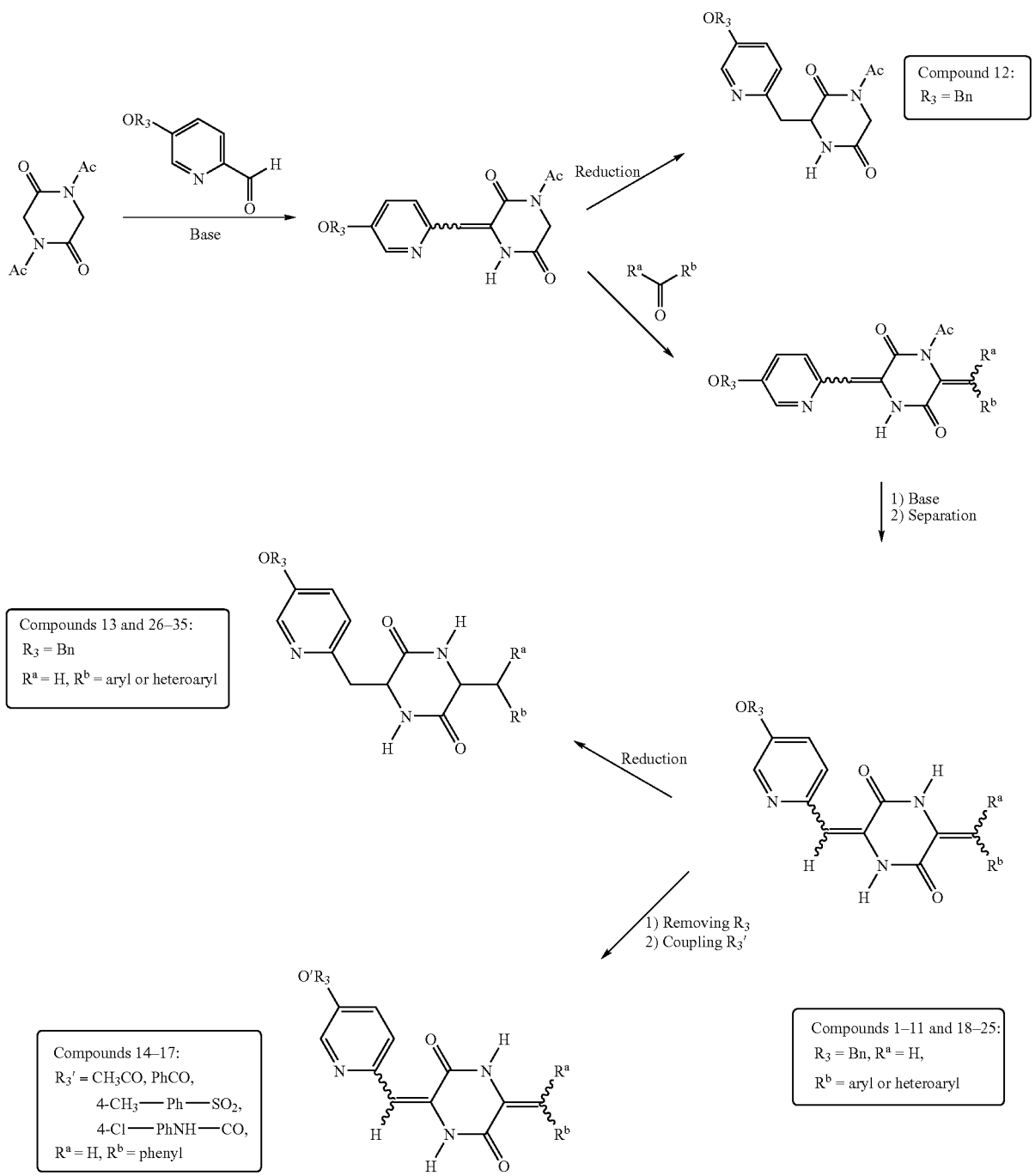

Details of synthesis of Compounds 1-35 are described in Examples 1-35, respectively. To prepare other piperazinedione compounds, the pyridinyl (shown in the above scheme) can be replaced by an aryl or another heteroaryl (e.g., furyl, pyrrolyl, imidazolyl, pyrimidinyl, or indolyl), and one of the two acetyl groups (Ac) on the piperazinedione ring (also shown in the above scheme) can be replaced by another substituent (e.g., carbonyl, carbamido, carbamyl, or carboxyl).

The chemicals used in the above-described synthetic route may include, for example, solvents, reagents, catalysts, protecting group and deprotecting group reagents. The methods described above may additionally include steps, either before or after the steps described specifically herein, to add or remove suitable protecting groups in order to ultimately allow synthesis of a piperazinedione compound. In addition, various synthetic steps may be performed in an alternate sequence or order to give the desired piperazinedione compounds. Synthetic chemistry transformations and protecting group methodologies (protection and deprotection) useful in synthesizing applicable piperazinedione compounds are known in the art and include, for example, those described in R. Larock, *Comprehensive Organic Transformations*, VCH Publishers (1989); T. W. Greene and P. G. M. Wuts, *Protective Groups in Organic Synthesis*, 2d. Ed., John Wiley and Sons (1991); L. Fieser and M. Fieser, *Fieser and Fieser's Reagents for Organic Synthesis*, John Wiley and Sons (1994); and L. Paquette, ed., *Encyclopedia of Reagents for Organic Synthesis*, John Wiley and Sons (1995) and subsequent editions thereof.

A piperazinedione compound thus synthesized can be further purified by a method such as column chromatography, high-pressure liquid chromatography, or recrystallization.

Note that the piperazinedione compounds contain at least two double bonds, and may further contain one or more asymmetric centers. Thus, they can occur as racemates and racemic mixtures, single enantiomers, individual diastereomers, diastereomeric mixtures, and cis- or trans- or E- or Z-double bond isomeric forms. All such isomeric forms are contemplated.

Also within the scope of this invention is a pharmaceutical composition contains an effective amount of at least one piperazinedione compound described above and a pharmaceutical acceptable carrier. Further, this invention covers a method of administering an effective amount of one or more of piperazinedione compounds to a subject with angiogenesis-related diseases. Such a subject can be identified by a health care professional based on results from any suitable diagnostic method.

The interrelationship of dosages for animals and humans (based on milligrams per meter squared of body surface) is described in Freireich et al., (1966) *Cancer Chemother Rep* 50: 219. Body surface area may be approximately determined from height and weight of the patient. See, e.g., Scientific Tables, Geigy Pharmaceuticals, Ardley, N.Y., 1970, 537. An effective amount of the piperazinedione compounds can range from about 0.1 mg/Kg to about 100 mg/Kg. Effective doses will vary, as recognized by those skilled in the art, depending on, e.g., the types of diseases treated, route of administration, excipient usage, and the possibility of co-usage with other therapeutic treatment.

To practice the method of the present invention, a composition having one or more of the above-mentioned compounds can be administered parenterally, orally, nasally, rectally, topically, or buccally. The term "parenteral" as used herein refers to subcutaneous, intracutaneous, intravenous, intramuscular, intraarticular, intraarterial, intrasynovial, intrasternal, intrathecal, intralesional, intraperitoneal, intratracheal or intracranial injection, as well as any suitable infusion technique.

A sterile injectable composition can be a solution or suspension in a non-toxic parenterally acceptable diluent or solvent, such as a solution in 1,3-butanediol. Among the acceptable vehicles and solvents that can be employed are mannitol, water, Ringer's solution, and isotonic sodium chloride solution. In addition, fixed oils are conventionally employed as a solvent or suspending medium (e.g., synthetic mono- or diglycerides). Fatty acid, such as oleic acid and its glyceride derivatives are useful in the preparation of injectables, as are natural pharmaceutically acceptable oils, such as olive oil or castor oil, especially in their polyoxyethylated versions. These oil solutions or suspensions can also contain a long chain alcohol diluent or dispersant, or carboxymethyl cellulose or similar dispersing agents. Other commonly used surfactants such as Tweens or Spans or other similar emulsifying agents or bioavailability enhancers which are commonly used in the manufacture of pharmaceutically acceptable solid, liquid, or other dosage forms can also be used for the purpose of formulation.

A composition for oral administration can be any orally acceptable dosage form including capsules, tablets, emulsions, and aqueous suspensions, dispersions, and solutions. In the case of tablets, commonly used carriers include lactose and corn starch. Lubricating agents, such as magnesium stearate, are also typically added. For oral administration in a capsule form, useful diluents include lactose and dried corn starch. When aqueous suspensions or emulsions are administered orally, the active ingredient can be suspended or dissolved in an oily phase combined with emulsifying or suspending agents. If desired, certain sweetening, flavoring, or coloring agents can be added.

A nasal aerosol or inhalation composition can be prepared according to techniques well known in the art of pharmaceutical formulation. For example, such a composition can be prepared as a solution in saline, employing benzyl alcohol or other suitable preservatives, absorption promoters to enhance bioavailability, fluorocarbons, and/or other solubilizing or dispersing agents known in the art. A composition having one or more active above-described compounds can also be administered in the form of suppositories for rectal administration.

A pharmaceutically acceptable carrier is routinely used with one or more active above-mentioned compounds. The carrier in the pharmaceutical composition must be "acceptable" in the sense that it is compatible with the active ingredient of the composition (and preferably, capable of stabilizing the active ingredient) and not deleterious to the subject to be treated. One or more solubilizing agents can be utilized as pharmaceutical excipients for delivery of an above-mentioned compound. Examples of other carriers include colloidal silicon oxide, magnesium stearate, cellulose, sodium lauryl sulfate, and D&C Yellow #10.

The piperazinedione compounds of this invention can be preliminarily screened for their efficacy in treating angiogenesis-related diseases by an in vitro assay (See Examples 36 and 37 below) and then confirmed by in vivo assay (See Example 38 below). Other methods will also be apparent to those of ordinary skill in the art.

The specific examples below are to be construed as merely illustrative, and not limitative of the remainder of the disclosure in any way whatsoever. Without further elaboration, it is believed that one skilled in the art can, based on the description herein, utilize the present invention to its fullest extent. All publications cited herein are hereby incorporated by reference in their entirety.

EXAMPLE 1

Synthesis of 3-[(5-benzyloxypyridin-2-yl)methylidene]-6-phenylmethylidene piperazine-2,5-dione (Compound 1).

1,4-Diacetyl-piperazine-2,5-dione (8.6 g) was added to a solution of 5-benzyoxypyridin-2-yl-formaldehyde (4.0 g) in 5.6 mL of triethylamine and 40 mL of dimethylformamide. The mixture was stirred at room temperature for 16 hr and then cooled at ice bath to produce a yellow precipitate. The precipitate was then collected and washed with ethyl acetate to give 5.4 g (77%) of 1-acetyl-3-[(5-benzyloxypyridin-2-yl)methylidene]piperazine-2,5-dione (Compound A).

mp: 189-191° C.

$^1$HNMR (400 MHz, DMSO): $\delta$2.52 (s, 3H), $\delta$4.54 (s, 3H), $\delta$4.33 (s, 2H), $\delta$5.25 (s, 2H), $\delta$6.85 (s, 1H), $\delta$7.384~$\delta$7.488

(m, 5H, aromatic), δ7.499 (d, J=8.8, 1H), δ7.689 (d, J=8.8, 1H), δ8.533 (s, 1H), and δ12.147 (s, 1H).

Compound A (3.51 g) was added to a 40 mL of dimethylformamide solution containing equal molar of benzaldehyde and 4 equivalents of triethylamine. The solution was refluxed at 60° C. for 16 hr and cooled at ice bath to produce a yellow precipitate. The precipitate was then collected and washed with ethyl acetate to give 3.3 g (83%) of the desired product 3-[(5-benzyloxypyridin-2-yl)methylidene]-6-phenylmethylidenepiperazine-2,5-dione (Compound 1) as a mixture of isomers. The mixture was predominately the ZZ and EZ isomers.

mp: 223-225° C. $^1$HNMR (400 MHz, DMSO): δ5.243 (s, 2H), δ6.695 (s, 1H), δ6.812 (s, 1H), δ7.346~δ7.634 (m, 12H, aromatic), δ8.528 (s, 1H), δ10.245 (s, 1H), and δ12.289 (s, 1H).

EXAMPLE 2

Synthesis of 3-[(5-benzyloxypyridin-2-yl)methylidene]-6-p-hydroxyphenyl methylidenepiperazine-2,5-dione (Compound 2).

Compound 2 was prepared in a similar manner as described in Example 1.

mp: 260-263° C. $^1$HNMR (400 MHz, DMSO): δ5.244 (s, 2H), δ6.669 (s, 1H), δ6.753 (s, 1H), δ6.798 (s, 1H, aromatic), δ6.819 (s, 1H, aromatic), δ7.347~δ7.647 (m, 9H, aromatic), δ9.821 (s, 1H), δ10.064 (s, 1H), and δ12.216 (s, 1H).

EXAMPLE 3

Synthesis of 3-[(5-benzyloxypyridin-2-yl)methylidene]-6-p-methoxyphenyl methylidenepiperazine-2,5-dione (Compound 3).

Compound 3 was prepared in a similar manner as described in Example 1.

mp: 238-240° C. $^1$HNMR (400 MHz, DMSO): δ5.244 (s, 2H), δ6.669 (s, 1H), δ6.753 (s, 1H), δ6.798 (s, 1H, aromatic), δ6.819 (s, 1H, aromatic), δ7.347~δ7.647 (m, 9H, aromatic), δ9.821 (s, 1H), δ10.064 (s, 1H), and δ12.216 (s, 1H).

EXAMPLE 4

Synthesis of 3-[(5-benzyloxypyridin-2-yl)methylidene]-6-p-fluorophenyl methylidenepiperazine-2,5-dione (Compound 4).

Compound 4 was prepared in a similar manner as described in Example 1.

mp: 242-244° C. $^1$HNMR (400 MHz, DMSO): δ5.237 (s, 2H), δ6.688 (s, 1H), δ6.794 (s, 1H), δ7.209~δ7.624 (m, 11H, aromatic), δ8.520 (s, 1H), δ10.348 (s, 1H), and δ12.279 (s, 1H).

EXAMPLE 5

Synthesis of 3-[(5-benzyloxypyridin-2-yl)methylidene]-6-p-chlorophenyl methylidenepiperazine-2,5-dione (Compound 5).

Compound 5 was prepared in a similar manner as described in Example 1.

mp: 250-251° C.

EXAMPLE 6

Synthesis of 3-[(5-benzyloxypyridin-2-yl)methylidene]-6-p-benzyoxphenylmethylidene piperazine-2,5-dione (Compound 6).

Compound 6 was prepared in a similar manner as described in Example 1.

mp: 253-255° C. $^1$HNMR (400 MHz, DMSO): δ5.142 (s, 2H), δ5.235 (s, 2H), δ6.672 (s, 1H), δ6.777 (s, 1H), δ7.041~δ7.639 (m, 16H, aromatic), δ8.520 (s, 1H), δ10.180 (s, 1H), and δ12.235 (s, 1H).

EXAMPLE 7

Synthesis of 3-[(5-benzyloxypyridin-2-yl)methylidene]-6-[(furan-2-yl)methylidene]piperazine-2,5-dione (Compound 7).

Compound 7 was prepared in a similar manner as described in Example 1.

mp: 256-257° C. $^1$HNMR (400 MHz, DMSO): δ5.245 (s, 2H), δ6.656 (d, J=1.6, 1H), δ6.664 (d, J=1.6, 1H), δ6.685 (s, 1H), δ6.720 (s, 1H), δ7.349~δ7.942 (m, 8H, aromatic), δ8.527 (s, 1H), δ9.515 (s, 1), and δ12.312 (s, 1H).

EXAMPLE 8

Synthesis of 3-[(5-benzyloxypyridin-2-yl)methylidene]-6-[(thien-2-yl)methylidene]piperazine-2,5-dione (Compound 8).

Compound 8 was prepared in a similar manner as described in Example 1.

mp: 215-217° C. $^1$HNMR (400 MHz, DMSO): δ5.245 (s, 2H), δ6.716 (s, 1H), δ6.974 (s, 1H), δ7.186 (s, 1H), δ7.384~δ7.746 (m, 9H, aromatic), δ8.525 (s, 1H), δ9.753 (s, 1H), and δ12.288 (s, 1H).

EXAMPLE 9

Synthesis of 3-[(5-benzyloxypyridin-2-yl)methylidene]-6-[(2-pyridinyl)methylidene]piperazine-2,5-dione (Compound 9).

Compound 9 was prepared in a similar manner as described in Example 1.

mp: 248-250° C. $^1$HNMR (400 MHz, DMSO): δ5.246 (s, 2H), δ6.709 (s, 1H), δ6.788 (s, 1H), δ7.349~δ7.661 (m, 8H, aromatic), δ7.923 (d, J=8, 1H, aromatic), δ8.473 (d, J=3.6, 1H), δ8.533 (d, J=2.8, 1H), δ8.680 (d, J=2, 1H), δ10.667 (s, 1H), and δ12.324 (s, 1H).

EXAMPLE 10

Synthesis of 3,6-di[(5-benzyloxypyridin-2-yl)methylidene]piperazine-2,5-dione (Compound 10).

Compound 10 was prepared in a similar manner as described in Example 1.

mp: 283-285° C. $^1$HNMR (400 MHz, DMSO): δ5.145 (s, 4H), δ6.780 (s, 2H), δ7.240~δ7.394 (m, 14H, aromatic), δ8.381 (s, 2H), δ10.145 (s, 1H), and δ12.58 (s, 1H).

EXAMPLE 11

Synthesis of 3-[(5-benzyloxypyridin-2-yl)methylidene]-6-(2-oxo-3-indolylidene)piperazine-2,5-dione (Compound 11).

Compound 11 was prepared in a similar manner as described in Example 1.
mp: >300° C.

EXAMPLE 12

Synthesis of 1-acetyl-3-[(5-benzyloxypyridin-2-yl)methyl]piperazine-2,5-dione (Compound 12)

A suspension of 3.51 g of 1,4-diacetyl-piperazine-2,5-dione and excess of zinc powder in a mixture of 100 mL of acetic acid and 10 mL of water was stirred and refluxed for 5-10 minutes and cooled. The mixture was filtered. The solid thus obtained was collected and washed with water to give 2.0 g of the desired 1-acetyl-3-[(5-benzyloxypyridin-2-yl)methyl]piperazine-2,5-dione (Compound 12).
mp: 215-216° C.

EXAMPLE 13

Synthesis of 3,6-di[(5-benzyloxypyridin-2-yl)methyl]piperazine-2,5-dione (Compound 13).

A suspension of 3,6-di[(5-benzyloxypyridin-2-yl)methylidene]piperazine-2,5-dione (Compound 10; 0.2 g) and excess of zinc powder in a mixture of 10 mL of acetic acid and 10 mL of water was stirred and refluxed for 5-10 minutes and filtered while hot. Water was added to dissolve zinc acetate. The filtrate was concentrated and filtered. The solid thus obtained was collected and washed with water to give 80 mg (40%) of the desired 3,6-di[(5-benzyloxypyridin-2-yl)methyl]piperazine-2,5-dione (Compound 13).
mp: 228-231° C.

EXAMPLE 14

Synthesis of 3-[(5-acetoxypyridin-2-yl)methylidene]-6-(benzylmethylidene)piperazine-2,5-dione (Compound 14).

3-[(5-benzyloxypyridin-2-yl)methylidene]-6-(benzylmethylidene)piperazine-2,5-dione (Compound 1, 0.5 g, 1.26 mmol) and NaOH (0.5 g, 12.5 mmol) were dissolved in 100 mL of methanol. The mixture was hydrogenated with 0.5 g palladium/charcoal under 1 atmospheric pressure. After completing the reaction as monitored by TLC, the catalyst was removed by filtration and the filtrate was evaporated in vacuo to produce a reside. The residue was added with 50 mL water and the obtained aqueous solution was adjusted to pH=7. A precipitated was formed and collected to obtain a 0.27 g product of 3-[(5-hydroxypyridin-2-yl)methylidene]-6-(benzylmethylidene)piperazine-2,5-dione (Compound B) (70% yield).
$^1$HNMR (400 MHz, CDCl$_3$): δ6.758 (s, 1H), δ7.087 (s, 1H), δ7.290~δ7.580 (m, 7H, aromatic), δ8.328 (s, 1H), and δ12.289 (s, 1H).
A solution of compound B (0.05 g, 0.16 mmole) in acetic anhydride (50 mL) was refluxed at 150° C. for 24 hrs. The unreacted acetic anhydride and produced acetic acid were removed in vacuo to obtain a residue. The residue was chromatographied using silica gel column with a developing solvent (CH$_2$Cl$_2$:MeOH=9:1) to give 0.051 g (90%) of Compound 14 as a mixture of isomers. The mixture was predominately the ZZ isomer.
$^1$HNMR (400 MHz, CDCl$_3$): δ2.377 (s, 3H), δ6.786 (s, 1H), δ7.107 (s, 1H), δ7.368~δ8.496 (m, 7H, aromatic), δ8.224 (s, 1H), and δ12.498 (s, 1H).

EXAMPLE 15

Synthesis of 3-[(5-benzoyloxypyridin-2-yl)methylidene]-6-(benzylmethylidene)piperazine-2,5-dione (Compound 15).

Compound 15 was prepared in a similar manner as described in Example 14.
$^1$HNMR (400 MHz, CDCl$_3$): δ6.786 (s, 1H), δ7.107 (s, 1H), δ7.368~δ8.496 (m, 13H, aromatic), and δ8.223 (s, 1H).

EXAMPLE 16

Synthesis of 3-[(5-(4-toluenesulfonyl)pyridin-2-yl)methylidene]-6-(benzylmethylidene)piperazine-2,5-dione (Compound 16).

Compound 16 was prepared in a similar manner as described in Example 14.
$^1$HNMR (400 MHz, CDCl$_3$): δ2.503 (s, 3H), δ6.751 (s, 1H), δ7.102 (s, 1H), δ7.343~δ8.159 (m, 12H, aromatic), δ8.223 (s, 1H), and δ12.315 (s, 1H).

EXAMPLE 17

Synthesis of 3-[(5-(4-chlorophenylcarbamic)pyridin-2-yl)methylidene]-6-(benzylmethylidene)piperazine-2,5-dione (Compound 17).

Compound 17 was prepared in a similar manner as described in Example 14.

EXAMPLE 18

Synthesis of 3-(5-benzyloxy-pyridin-2-ylmethylene)-6-(4-nitro-benzylidene)-piperazine-2,5-dione (Compound 18).

Compound 18 was prepared in a similar manner as described in Example 1.
mp: >300° C.

EXAMPLE 19

Synthesis of 3-(5-benzyloxy-pyridin-2-ylmethylene)-6-(2-nitro-benzylidene)-piperazine-2,5-dione (Compound 19).

Compound 19 was prepared in a similar manner as described in Example 1.
mp: 295-296° C.

EXAMPLE 20

Synthesis of 3-(5-benzyloxy-pyridin-2-ylmethyl-ene)-6-(3-chloro-benzylidene)-piperazine-2,5-dione (Compound 20).

Compound 20 was prepared in a similar manner as described in Example 1.
mp: 236-237° C.

EXAMPLE 21

Synthesis of 3-(5-benzyloxy-pyridin-2-ylmethyl-ene)-6-(3,5-dimethoxy-benzylidene)-piperazine-2,5-dione (Compound 21).

Compound 21 was prepared in a similar manner as described in Example 1.
mp: 237-239° C.

EXAMPLE 22

Synthesis of 3-(5-benzyloxy-pyridin-2-ylmethyl-ene)-6-(3,4-dichloro-benzylidene)-piperazine-2,5-dione (Compound 22).

Compound 22 was prepared in a similar manner as described in Example 1.
mp: 264-265° C.

EXAMPLE 23

Synthesis of 3-benzo[1,3]dioxol-5-ylmethylene-6-(5-benzyloxy-pyridin-2-ylmethylene)-piperazine-2,5-dione (Compound 23).

Compound 23 was prepared in a similar manner as described in Example 1.
mp: 255-256° C.

EXAMPLE 24

Synthesis of 3-(5-benzyloxy-pyridin-2-ylmethyl-ene)-6-(3-hydroxy-benzylidene)-piperazine-2,5-dione (Compound 24).

Compound 24 was prepared in a similar manner as described in Example 1.

EXAMPLE 25

Synthesis of 3-(5-benzyloxy-pyridin-2-ylmethyl-ene)-6-(3,5-dihydroxy-benzylidene)-piperazine-2,5-dione (Compound 25).

Compound 25 was prepared in a similar manner as described in Example 1.

EXAMPLE 26

Synthesis of 3-benzyl-6-(5-benzyloxy-pyridin-2-ylmethyl)-piperazine-2,5-dione (Compound 26).

Compound 26 was prepared in a similar manner as described in Example 13 except that Compound 1 was used as a starting material.
mp: 215-218° C.

EXAMPLE 27

Synthesis of 3-(5-benzyloxy-pyridin-2-ylmethyl)-6-(4-hydroxy-benzyl)-piperazine-2,5-dione (Compound 27).

Compound 27 was prepared in a similar manner as described in Example 13 except that Compound 2 was used as a starting material.
mp: 229-231° C.

EXAMPLE 28

Synthesis of 3-(5-benzyloxy-pyridin-2-ylmethyl)-6-(4-methoxy-benzyl)-piperazine-2,5-dione (Compound 28).

Compound 28 was prepared in a similar manner as described in Example 13 except that Compound 3 was used as a starting material.
mp: 172-176° C.

EXAMPLE 29

Synthesis of 3-(5-benzyloxy-pyridin-2-ylmethyl)-6-(4-fluoro-benzyl)-piperazine-2,5-dione (Compound 29).

Compound 29 was prepared in a similar manner as described in Example 13 except that Compound 4 was used as a starting material.
mp: 220-222° C.

EXAMPLE 30

Synthesis of 3-(5-benzyloxy-pyridin-2-ylmethyl)-6-(4-chloro-benzyl)-piperazine-2,5-dione (Compound 30).

Compound 30 was prepared in a similar manner as described in Example 13 except that Compound 5 was used as a starting material.
mp: 227-229° C.

EXAMPLE 31

Synthesis of 3-(4-benzyloxy-benzyl)-6-(5-benzyloxy-pyridin-2-ylmethyl)-piperazine-2,5-dione (Compound 31).

Compound 31 was prepared in a similar manner as described in Example 13 except that Compound 6 was used as a starting material.
mp: 200-202° C.

EXAMPLE 32

Synthesis of 3-(5-benzyloxy-pyridin-2-ylmethyl)-6-furan-2-ylmethyl-piperazine-2,5-dione (Compound 32).

Compound 32 was prepared in a similar manner as described in Example 13 except that Compound 7 was used as a starting material.
mp: 210-212° C.

EXAMPLE 33

Synthesis of 3-(5-benzyloxy-pyridin-2-ylmethyl)-6-thiophen-2-ylmethyl-piperazine-2,5-dione (Compound 33).

Compound 33 was prepared in a similar manner as described in Example 13 except that Compound 8 was used as a starting material.
mp: 201-203° C.

EXAMPLE 34

Synthesis of 3-(5-benzyloxy-pyridin-2-ylmethyl)-6-pyridin-3-ylmethyl-piperazine-2,5-dione (Compound 34).

Compound 34 was prepared in a similar manner as described in Example 13 except that Compound 9 was used as a starting material.
mp: 193-196° C.

EXAMPLE 35

Synthesis of 3-[(5-benzyloxypyridin-2-yl)methyl]-6-(2-oxo-3-indolyl)piperazine-2,5-dione (Compound 35).

Compound 35 was prepared in a similar manner as described in Example 13 except that Compound 11 was used as a starting material.
mp: >243° C.

Example 36

Inhibition of Cell Proliferation

Human umbilical vein endothelial cells (HUVECs) were inoculated into 96 well microtiter plates in a volume of 100 µL at plating density of 10,000 cells/well. After cell inoculation, the microtiter plates were incubated at 37° C. in 5% $CO_2$/95% air having 100% relative humidity for 24 hours, and then the cells were incubated in M199/2% fetal bovine serum for another 24 hours prior to addition of test compounds. 1000-Fold stock solutions were prepared by dissolving test compounds in dimethyl sulfoxide and then stored frozen prior to use. Before adding a test compound, an aliquot of a frozen stock solution was thawed and diluted to the desired test concentration. Aliquots of 100 µL of test compound solutions were added to the appropriate microtiter wells. After 20-hour incubation, a [$^3$H]thymidine solution (2 µCi/mL, Amersham Pharmacia) was added to the cells and the microtiter plates were incubated for another 4 hours. Then, the cells were washed and harvested with Filter-Mate (Packard), and the amount of [$^3$H]thymidine incorporated in the cells was determined.

Compounds 1-9, 11, 18-23, and 26-35 were tested. Unexpectedly, a large number of them inhibited HUVECs proliferation.

EXAMPLE 37

Tube Formation Assay

HUVECs were inoculated into slide chambers, which were pre-coated with Matrigel in a 500 µL/well medium at plating density of $2 \times 10^5$ cells/well. After cell inoculation, vascular endothelium growth factor (VEGF) and test compounds was added to the cells. The chambers were incubated at 37° C. in 5% $CO_2$/95% air having 100% relative humidity for 24 hours. After incubation, tube formation was detected by microscopy (Nikon). For better observation, a MTT (3-[4,5-dimethylthiazol-2-yl]-2,5-diphenyltetrazolium bromide) solution with a concentration of 0.5 mg/mL was added and the chambers were incubated for another 1 hour prior to the microscopic detection.

Compounds 1-9, 11, 18-23, and 26-35 were tested. Unexpectedly, most of them inhibited tube formation induced by VEGF and some exerted complete inhibition.

EXAMPLE 38

Anti-Angiogenic Activities in Nude Mice Models

Matrigel (500 µL) containing vehicle or VEGF (150 ng/mL) was subcutaneously injected into mice. Test compounds were orally administered at a predetermined dose for six days. The mice were then sacrificed with intraperitoneal administration of pentobarbital. Matrigel plug thus formed was carefully clipped for histological examination. Inhibition of angiogenesis was determined using a hemoglobin assay kit. Briefly, the Matrigel plug was gently and homogenized for a short period of time, and then 20 µL whole blood was added into 5 mL Drabkin's solution (provided together with the hemoglobin assay kit). After 15 minutes at room temperature, optimal absorbance was obtained using colorimetric method at 530-550 nm. Hemoglobin concentration was calculated relative to a hemoglobin standard.

Compounds 1, 8, 9, 21, 22, and 24 were tested. Results showed that all of them inhibited angiogenesis in a concentration dependent manner. Specifically, 4 compounds showed $ID_{50}$ values less than 1 mg/kg and 2 compounds showed $ID_{50}$ values less than 3 mg/kg.

OTHER EMBODIMENTS

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. Thus, other embodiments are also within the scope of the following claims.

What is claimed is:
1. A compound having the formula:

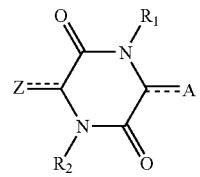

wherein

A is C(R$^a$R$^b$′) and ---- is a double bond;

Z is R$_3$O-(Ar)-C(R$^e$) and ---- is a double bond; in which Ar is pyridyl linked to C at position 2; and R$_3$ is C$_1$-C$_6$ alkyl substituted with aryl, C(O)R$^f$, or S(O)R$^f$;

each of R$_1$ and R$_2$, independently, is H or C(O)R$^g$;

R$^a$′ is benzo[1,3]dioxol-5-yl; and R$^b$′ is H, C$_1$-C$_6$ alkyl, or aryl;

each of R$^e$ and R$^f$, independently, is H, C$_1$-C$_6$ alkyl, aryl, or arylamino; and R$^g$ is H, C$_1$-C$_6$ alkyl, or aryl.

2. The compound of claim 1, wherein R$^b$′ is H.

3. The compound of claim 2, wherein R$_e$ is H.

4. The compound of claim 3, wherein R$_3$ is benzyl.

5. The compound of claim 4, wherein the compound is

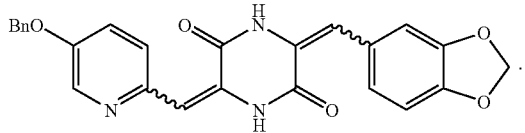

* * * * *